United States Patent
Goldstein et al.

(10) Patent No.: US 6,783,734 B1
(45) Date of Patent: Aug. 31, 2004

(54) CONVEX GEOMETRY ADHESIVE FILM SYSTEM FOR LASER CAPTURE MICRODISSECTION

(75) Inventors: Seth R. Goldstein, Bethesda, MD (US); Robert F. Bonner, Bethesda, MD (US); Paul D. Smith, Bethesda, MD (US); John Peterson, Bethesda, MD (US); Thomas Pohida, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/387,810

(22) Filed: Sep. 1, 1999

Related U.S. Application Data

(62) Division of application No. 08/883,821, filed on Jun. 27, 1997, now Pat. No. 6,100,051.

(51) Int. Cl.[7] .................................................. B01L 11/00
(52) U.S. Cl. ........................ 422/101; 422/68.1; 422/99; 435/284.1; 435/307.1; 435/309.1; 436/63; 436/174; 436/175; 436/177
(58) Field of Search .............................. 422/55, 57, 99, 422/103; 436/501, 503, 524, 525, 164, 165, 169, 174, 177; 356/36, 38, 44, 73.1, 335; 359/708

(56) References Cited

U.S. PATENT DOCUMENTS

| | | | |
|---|---|---|---|
| 1,965,861 A | * | 1/1934 | Schneider .................... 128/304 |
| 4,334,844 A | * | 6/1982 | Tanaka ........................... 425/2 |
| 4,624,915 A | | 11/1986 | Schindler et al. |
| 4,629,687 A | | 12/1986 | Schindler et al. |

(List continued on next page.)

FOREIGN PATENT DOCUMENTS

| | | |
|---|---|---|
| WO | WO 97/13838 | 4/1997 |

*Primary Examiner*—Jill Warden
*Assistant Examiner*—Dwayne K Handy
(74) *Attorney, Agent, or Firm*—William Michael Hynes; Townsend and Townsend and Crew LLP

(57) ABSTRACT

A tissue sample is conventionally visualized in a microscope. A selectively activated convex surface is provided, preferably at the distal end of a rod. This selectively activated convex surface when activated, typically with a laser through an optic light path in the microscope, provides the activated region with adhesive properties. At least one portion of the tissue sample which is to be extracted is identified. This identified portion is contacted with a portion of the selectively activated convex surface on the end of the rod. When the convex surface is activated, typically by exposure to laser light in the footprint of the desired sample, an adhesive transfer surface on the selectively activated convex surface is provided which adheres to the desired cells in the footprint of the desired sample. Thereafter, the adhesive transfer surface is separated from the remainder of the tissue sample while maintaining adhesion with the desired cells. Thus the desired portion of the tissue sample is extracted. The disclosed selectively activated convex surface is preferably utilized to collect desired tissue samples at more than one location on the same slide or from different slides. The collected tissue samples can thereafter be inspected if desired, as collected on the convex surface, and then liberated—as by dissolving the proteins of the samples. This can effectively concentrate rarely occurring cells in order to obtain enough pure material for analysis. A rod having a convex surface with the selectively activated material is set forth as a staple for use with the apparatus and process. Preferred shapes for the convex surface are disclosed as well as a method for coating rods with a resultant rod article.

7 Claims, 5 Drawing Sheets

U.S. PATENT DOCUMENTS

| | | | | |
|---|---|---|---|---|
| 4,807,597 A | * | 2/1989 | Tsuno et al. | 128/6 |
| 5,084,005 A | * | 1/1992 | Kachigan | 604/1 |
| 5,202,230 A | | 4/1993 | Kamentsky | |
| 5,295,982 A | * | 3/1994 | Schatz | 604/313 |
| 5,541,064 A | | 7/1996 | Bacus et al. | |
| 5,665,582 A | | 9/1997 | Kausch et al. | |
| 5,723,290 A | | 3/1998 | Eberwine et al. | |
| 5,759,781 A | | 6/1998 | Ward et al. | |
| 5,817,462 A | | 10/1998 | Garini et al. | |
| 5,843,644 A | | 12/1998 | Liotta et al. | |
| 5,843,657 A | | 12/1998 | Liotta et al. | |
| 5,859,699 A | | 1/1999 | Baer et al. | |
| 5,994,149 A | * | 11/1999 | Robinson et al. | 436/518 |
| 6,027,493 A | * | 2/2000 | Donitzky et al. | 606/4 |
| 6,060,288 A | * | 5/2000 | Adams et al. | 435/91.2 |
| 6,110,749 A | * | 8/2000 | Obremski et al. | 436/527 |
| 6,174,424 B1 | * | 1/2001 | Wach et al. | 205/73 |
| 6,231,597 B1 | * | 5/2001 | Deem et al. | 623/1.12 |
| 6,251,688 B1 | * | 6/2001 | Erb et al. | 436/518 |
| 6,277,637 B1 | * | 8/2001 | Lintilhac et al. | 435/410 |

\* cited by examiner

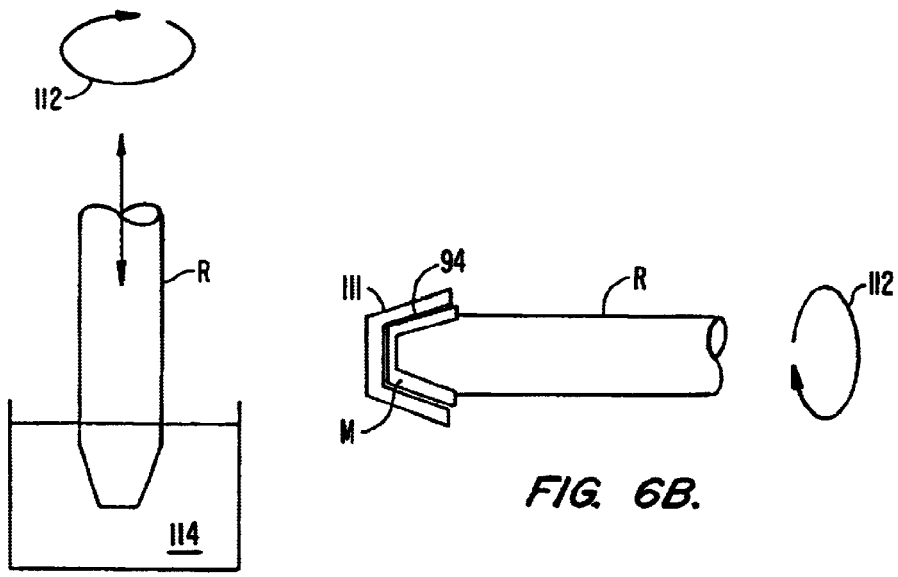
FIG. 6A.
FIG. 6B.
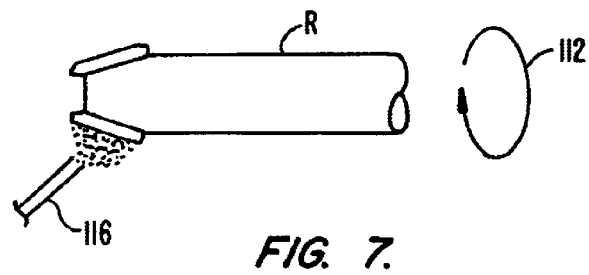
FIG. 7.
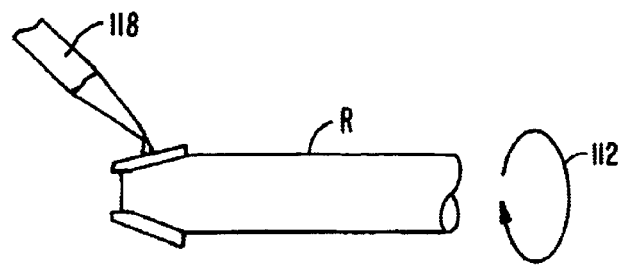
FIG. 8.

CONVEX GEOMETRY ADHESIVE FILM SYSTEM FOR LASER CAPTURE MICRODISSECTION

This application is a divisional of and claims the benefit of U.S. patent application Ser. No. 08/883,821, filed Jun. 27, 1997 now U.S. Pat. No. 6,100,051.

This disclosure deals with a convex geometry for the laser actuated adhesive film used to perform Laser Capture Microdissection (LCM)—a technique for removing minute amounts of tissue from pathology slides in a convenient, rapid manner. Several configurations for solving a variety of problems encountered in LCM are described, as well as a mechanical mechanism for performing some of the mechanical functions involved in the procedure.

BACKGROUND OF THE INVENTION

Specifically, many diseases are now understood at the molecular and genetic level. Analysis of such molecules is important for disease diagnosis and prognosis. Current methods for direct extraction of cellular tissue material from a tissue sample are limited because the extraction reflects only the average content of disease associated markers. In reality, tissues are very heterogeneous and the most diagnostic portions of the tissue may be confined to a few hundred cells or less in a lesion. Thus molecular analysis of human pathology sections will require the targeting and removal of pure populations of homogeneous cells from within a specimen where these cells may comprise only a few percent of the total local tissue or even much less (e.g., 1 cell in a 1000 or even less). The modification of the LCM invention covered in this application is particularly important in the collection of sparse or rare cells within a tissue and cases where such cells must be collected from a variety of specimens in order to provide sufficient material for an accurate statistical representation of the pathology. Examples include isolation cells that were infected by an AIDS virus, macrophages containing an infectious tuberculosis bacteria, cells within a kidney glomerulus in patients exhibiting proteinuria, brain cells and plaques in brain exhibiting Alzheimer's Syndrome, as well as cancerous tissues. In each case the precise molecular description of the variant of the disease which might be related to different natural etiology and responses of that particular patient to different therapies can only be accomplished without gross contamination of molecules from surrounding cells. Though we specifically discuss how laser microdissection is critical in the molecular analysis of cancer, the same principles apply to a molecular description (e.g., DNA mutations, alterations of gene expression, and post-transcriptional modification of proteins) of a variety of diseases and their response to drug treatment and of normal human developing and aging.

Normal tissue samples contain a variety of cell types surrounding and adjacent to the pre-invasive and invasive tumor cells. A region of the tumor tissue subject to biopsy and diagnosis as small as 1.0 mm can contain normal epithelium, pre-invasive stages of carcinoma, in-situ carcinoma, invasive carcinoma, and inflammatory areas. Consequently, routine scraping and cutting methods will gather all of these types of cells, and hence, loss of an allele will be masked by presence of a normal copy of the allele in the contaminating non-malignant cells. Existing methods for cutting away or masking a portion of tissue do not have the needed resolution. Hence the analysis of genetic results by those previous methods are always plagued by contaminating alleles from normal cells, undesired cells or vascular cells.

The molecular study of human tumors is currently limited by the techniques and model systems available for their characterization. Studies to quantitatively or qualitatively assess proteins or nucleic acid expression in human tumor cells are compromised by the diverse cell populations present in bulk tumor specimens. Histologic fields of invasive tumor typically show a number of cell types including tumor cells, stromal cells, endothelial cells, normal epithelial cells and inflammatory cells. Since the tumor cells are often a relatively small percentage of the total cell population it is difficult to interpret the significance of net protein or nucleic acid alterations in these specimens.

Studies of human tumor cells in culture do not account for the complex interactions of the tumor cells with host cells and extracellular matrix, and how they may regulate tumor cell protease productivity or activation. Immunohistochemical staining allows one to examine enzyme distribution in regions of tumor invasion, however, results vary with tissue fixation and antibody-antigen affinity, and provide only a semi-quantitative assessment of protein levels. Furthermore, quantitative interpretation of staining results is complicated by the variability of staining patterns within tissue sections, subjective evaluation of staining intensity, and the difficulty in interpreting the significance of stromal staining. In addition, many antibodies utilized in the study of proteases do not differentiate pro-enzyme from active enzyme species. Assays of enzyme or mRNA levels from homogenates of human tumors does not account for either the mixed population of cells within the specimens, or the concomitant pathophysiologic processes which may occur in the tissue.

Prior methods of study have not allowed investigators to specifically examine genetic alterations in pre-invasive lesions. Even the most sophisticated genetic testing techniques to date have been of limited value because the input DNA, RNA or proteins to be analyzed are not derived from pure cell populations exhibiting the disease morphology. Several methods have been reported for tissue microdissection to address this problem. These include gross dissection of frozen tissue blocks to enrich for specific cell populations, irradiation of manually ink stained sections to destroy unwanted genetic material, touch preparations of frozen tissue specimens and microdissection with manual tools. These methods, however, are not sufficiently precise and efficient for routine research or high throughput clinical molecular diagnostic applications. Manual microdissection, for example, has good precision but is time consuming, labor intensive, requires a high degree of manual dexterity, and is not generally suitable for the ordinary technologist.

In Lance A. Liotta et al. U.S. Provisional Patent Application Serial No. 60/036,927 filed Feb. 7, 1997, entitled Isolation of Cellular Material Under Microscope Visualization, there is described a technique that we have come to call Laser Capture Microdissection (LCM). Simply stated, a method and apparatus was disclosed in which a tissue sample was provided, typically on a slide under observation in a microscope. The tissue was contacted with a selectively activated surface which could be activated to provide selective regions thereof with adhesive properties. The tissue sample is visualized through a microscope and at least one portion of the tissue sample which is to be extracted is identified. Thereafter, the selectively activated surface is activated, typically by a laser routed through a fiber optic being directed onto the selectively activated surface in the footprint of the desired tissue. This is done while a region of selectively activated surface is in contact with the portion of the tissue sample selected. The activated region of the selectively activated surface adheres to that portion of the tissue sample. Thereafter, the activated surface is separated from the tissue sample while maintaining adhesion between the activated region of selectively activated surface and the portion of the tissue sample. The portion of the tissue sample is extracted from the remaining portion of said tissue sample.

While the basic technique disclosed in the above-entitled patent deals with applying a large free piece of EVA film to a tissue sample on a slide, the reduction of this technique to a practical method and apparatus which can be utilized by relatively untrained personnel with conventional microscopes is not set forth. Accordingly, in the following specification, one practical embodiment of this technique is set forth.

SUMMARY OF THE INVENTION

A tissue sample is conventionally visualized in a microscope. A selectively activated convex surface is provided, preferably at the distal end of a rod. This selectively activated convex surface when activated, typically with a laser through an optic light path in the microscope, provides the activated region with adhesive properties. At least one portion of the tissue sample which is to be extracted is identified. This identified portion is contacted with a portion of the selectively activated convex surface on the end of the rod. When the convex surface is activated, typically by exposure to laser light in the footprint of the desired sample, an adhesive transfer surface on the selectively activated convex surface is provided which adheres to the desired cells in the footprint of the desired sample. Thereafter, the adhesive transfer surface is separated from the remainder of the tissue sample while maintaining adhesion with the desired cells. Thus the desired portion of the tissue sample is extracted. The disclosed selectively activated convex surface is preferably utilized to collect desired tissue samples at more than one location on the same slide or from different slides. The collected tissue samples can thereafter be inspected if desired, as collected on the convex surface, and then liberated—as by dissolving the proteins of the samples. This can effectively concentrate occurring remaining cells in order to obtain enough pure material for analysis. A rod having a convex surface with the selectively activated material is set forth as a staple for use with the apparatus and process. Preferred shapes for the convex surface are disclosed as well as a method for coating rods with a resultant rod article.

BRIEF DESCRIPTION OF THE DRAWINGS

FIGS. 6A and 6B illustrate dipping and drying of a rod, FIG. 7 illustrates spray coating of a rod, and FIG. 8 illustrates application of a measured coating to a rod.

DESCRIPTION OF THE PREFERRED EMBODIMENT

Figure 1:
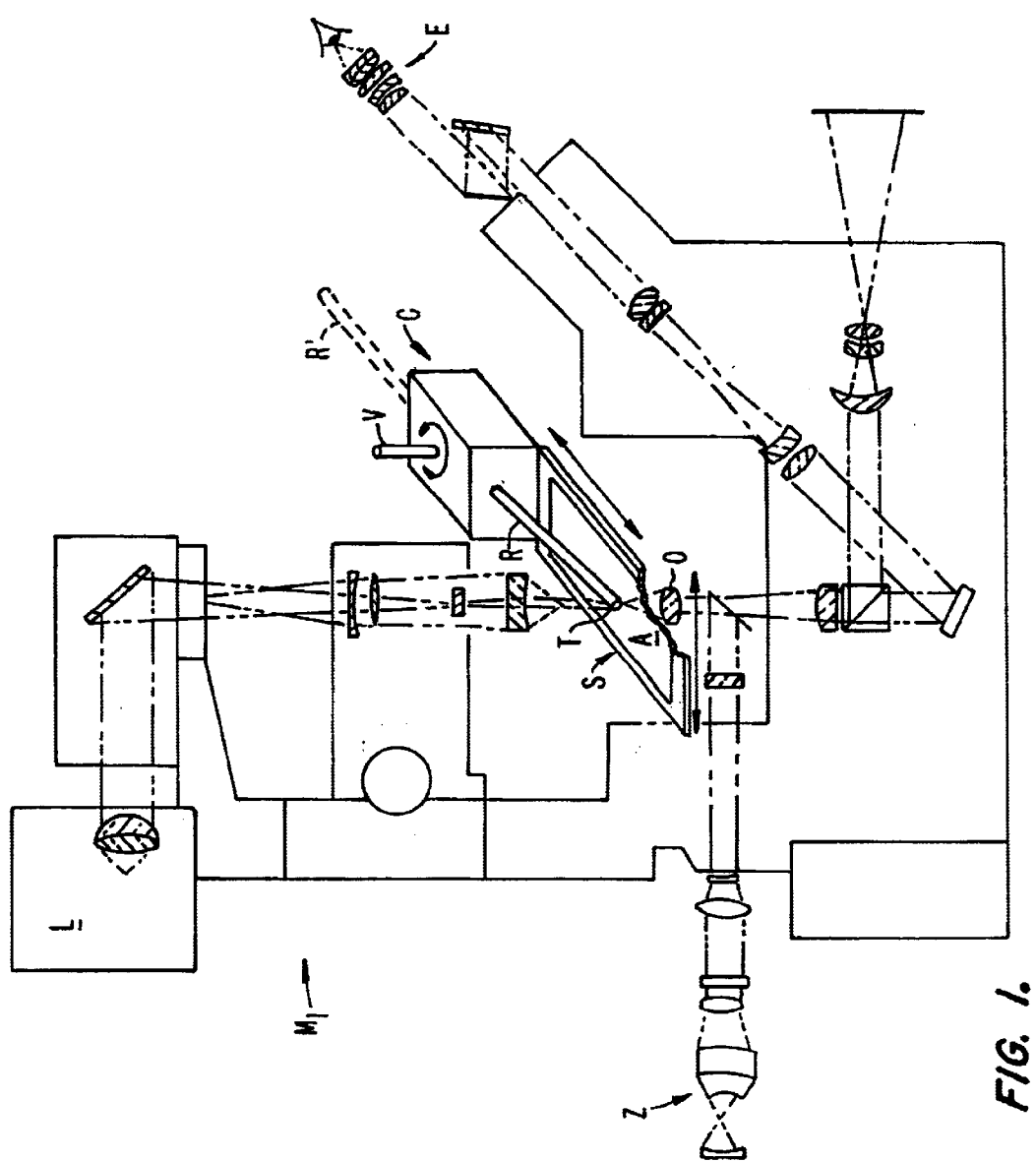
FIG. 1 is a side elevation view of a conventional inverted microscope having the convex geometry adhesive film system of this invention illustrated in solid lines for the collection of a sample by laser capture microdissection and illustrating in broken lines the pivoted position of the apparatus to permit convenient loading and unloading of a new rod out of the optical path.

Referring to FIG. 1, sample collector C is shown as an attachment to inverted microscope $M_I$. As is conventional, inverted microscope $M_I$ includes eyepiece E, objective O, conventional light source L all assisting in observing slide S having sample A.

Sample collector C is an attachment, only schematically shown in FIG. 1. It includes sample collecting rod R which is pivotal about vertical pivot axis V. Sample collecting rod R has coated collection tip T which is at the site on sample A of the desired cells to be collected.

Light Z from a laser enters the microscope through the epi-illumination port and is focused on the slide at a known, predetermined point, e.g. the center of the field of view.

In order to conveniently replace and remove the replenishable part of R, sample collecting rod R of sample collector C can be pivoted about axis V to move it out of the objective O to eyepiece E light path as shown by sample collecting rod R' in broken lines. This system will be more completely described with respect to FIG. 2.

Operation can be simply described. First the microscope stage is centered and the sample collecting rod R is placed in position above the slide. Next, slide S is inspected until desired cells, sample A are located. The slide is positioned on the stage so that sample A is at the center of the field. Then, sample collecting rod R having coated collection tip T is lowered by being pivoted about a horizontal axis using a mechanism that will be later explained in FIG. 2, so that contact occurs between collection tip T and sample A at the desired cells. Then, laser Z activates coated collection tip T and causes adhesion at the desired cells. If desired, small motions of the microscope stage can be used to position extended regions of A and the collection tip T in the laser beam in order to collect more than a single point of tissue of A corresponding to one laser spot. When all parts of the combination of A and tip T have been exposed to the laser, coated collection tip T with the desired cells adhered to it is then lifted off sample A, sample collecting rod R is rotated about its axis—only slightly—and the entire above process is repeated with a different sample, $A^1$.

Having grossly summarized the operation, description of the preferred embodiment will continue.

Figure 2A:
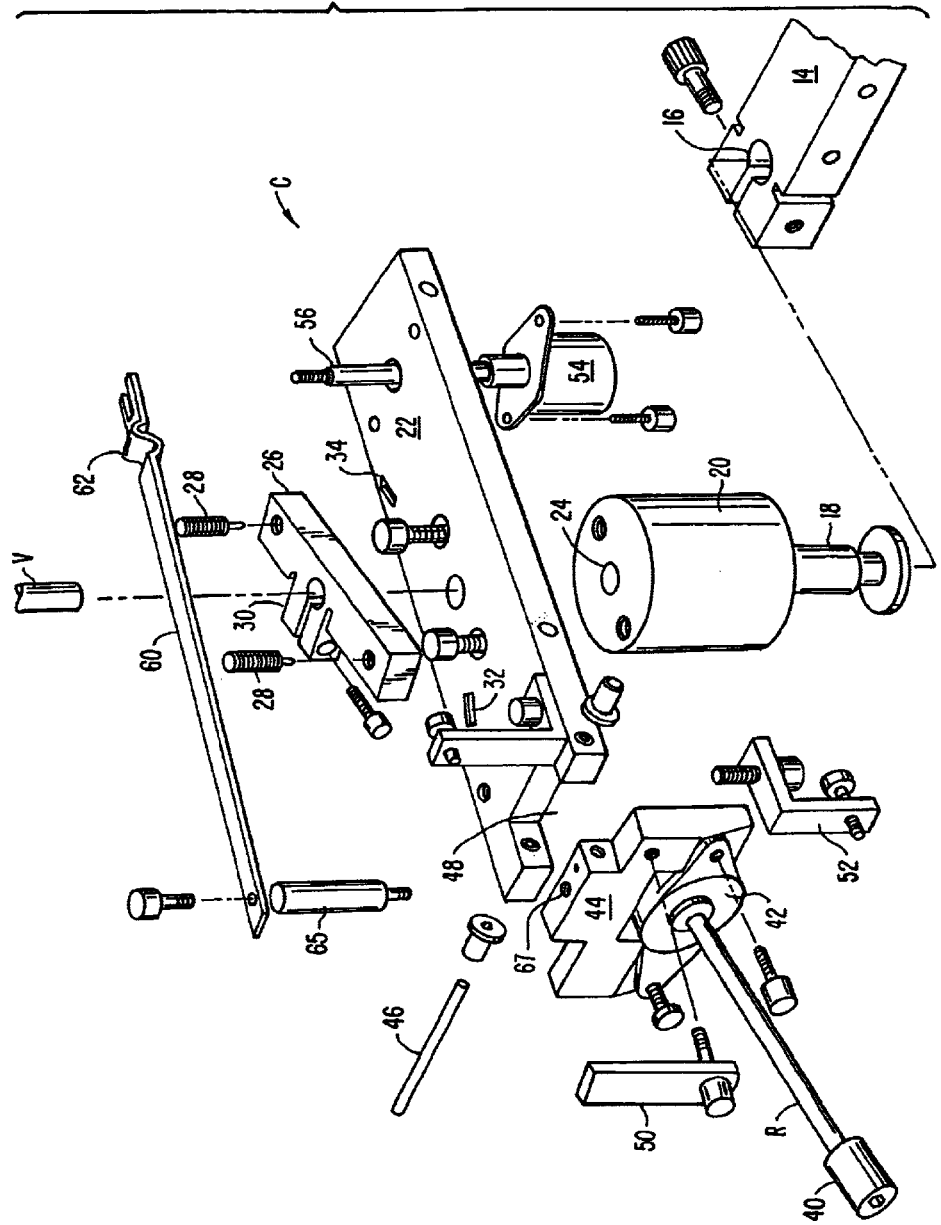
FIG. 2 is an exploded view of the mechanisms of the convex geometry ,adhesive film system of this invention without attachment to a microscope.

Referring to FIG. 2, sample collector C is shown together with part of sample collecting rod R. Stage mounting 14 mounts at split ring mounting 16 to main bushing 18. Main bushing 18 supports bearing block 20. Bearing block 20 in turn supports sample collector base 22. Vertical pivot axis V fits into bearing block 20 at bearing block central aperture 24 and is locked against relative rotation.

Detent block 26 locks to vertical pivot axis V and supports spring mounted detents 28. Locking of detent block 26 to vertical pivot axis V occurs at detent shaft lock 30.

Sample collector base 22 defines slide registering detent groove 32 and remote location detent groove 34. Simply stated, when sample collector base 22 is registered with spring mounted detents 28 overlying slide registering detent groove 32, sample collecting rod R with coated collection tip T overlies the central viewpoint of sample A on slide S. When the stage is centered this central view point coincides with the location of the laser beam. When sample collector base 22 is registered with spring mounted detents 28 overlying remote location detent groove 34, sample collecting rod R at coated collection tip T is away from slide S and its sample A permitting convenient loading and unloading of the replenishable part of rod R away from the slide S. (See FIG. 1.)

Sample collecting rod R as shown in FIG. 2 includes at its distal end coupling 40 for connection to various sequential sample collecting replenishable rod tips each with their own coated collection tip T. Such tips will be discussed later with respect to FIGS. 5A–5E. This same sample collecting rod R at the opposite end connects to rotational stepper motor 42. After each sample is collected on coated collection tip T, rotation by a small fraction of a full turn of rotational stepper motor 42 occurs until coated collection tip T has samples around the entire periphery (or less, if desired).

To avoid shearing the tissue and causing possible contamination, it is necessary that sample collecting rod R at coated collection tip T come out of contact with sample A on slide S before it is rotated. Accordingly, rotational stepper motor 42 is mounted to pivot block 44. Pivot block 44 in turn rocks about horizontal pivot shaft 46 within pivot aperture 48 at the end of sample collector base 22. Thus it will be seen that sample collecting rod R at coated collection tip T can move into and out of contact with sample A on slide S. After the rod has been rotated, the stage recentered, and the slide moved to a new position with desired cells at the center of the field, the rod is lowered.

The contact of coated collection tip T with sample A on slide S must be precisely controlled. This is done by using a leaf spring actuator to control the amount of force utilized for each contact of the sample collecting rod R.

This controlled contact of coated collection tip T at the end of sample collecting rod R is determined by vertical stepper motor 54 which attaches underneath sample collector base 22. Motor 54 having vertically extending stepper shaft 56 which upon motor actuation undergoes a linear vertical excursion. Vertically extending stepper shaft 56 fastens at the leaf spring 60 end adjacent linear expansion curve 62. At the opposite end, leaf spring 60 has pivot block bolt 65 which attaches to pivot block 44 at pivot block bolt aperture 67.

Having set forth this structure, operation of sample collector C to pivot sample collecting rod R at coated collection tip T into and out of contact with sample A on slide S can be easily understood. Specifically, vertical stepper motor 54 is moved in vertical excursion a controlled (e.g., computer) amount to carefully adjust the height of vertically extending stepper shaft 56. Stepper shaft 56 causes leaf spring 60 to tilt pivot block bolt 65. Pivot block bolt in turn pivots pivot block 44 and mounted rotational stepper motor 42 with attached sample collecting rod R. As rod R has coated collection tip T at the distal end, controlled touching of sample A can occur.

It will be understood the disclosed mechanism is extremely sensitive. Given the long lever arm of leaf spring 60, precision control over the force on sample A is easily achieved. Further, the amount of force utilized for the contact can control, within limits, the width of the "line" contact area of sample collected. Contact with reduced force will collect reduced amounts of sample A; contact with increased force will collect increased amounts of sample A.

In the positioning of desired cells of sample A on slide S for collection, two movements can be utilized. First, referring to FIG. 1, slide S can be provided with gross motion relative to conventional microscope stage S so as to center the sample A in the field of view. This sliding motion is well known to anyone who has operated a microscope.

Second, some minute movement of the conventional microscope stage 70 is desired for collecting desired cells located anywhere within the contact zone of R.

An alternative to raising and then rotating and then lowering the rod R is to roll the rod over the area A in conjunction with controlled motion of the stage so there is no shearing of the tissue.

An alternative to small stage motions is to scan the laser beam, turning it on and off so that only the desired cells and the adjacent adhesive are illuminated by the laser.

Having described sample collector C with sample collecting rod R and coated collection tip T, the operation of the tip with respect to the sample can now be set forth.

To evaluate some performance parameters for the cylindrical geometry concept, it is convenient to use the following parabolic approximation of a circle, good for small distances x:

$$y=(x^2)/2R$$

This approximates a circle of radius R whose center is at y=R and x=0 (e.g. its lowest point is at the origin which is assumed to be the point of contact between the rod/film and the tissue). If 2R=3/16 inch (=4.68 mm), then the circumference is 14.7 mm. In order for y to lift off by 50 microns (0.002 inches) to avoid contamination with the tissue at the next transfer site, x=0.48 mm using the above relation.

This would allow 30 transfers on a single rod assuming the entire periphery is used and the transfers are spaced 0.48 mm apart on centers. For visualization, if one allowed a maximum Y of 1 micron to maintain focus on the tissue while it is on the curved surface, the resulting X=0.070 mm. Thus a field of ≈140 microns wide will be in sharp focus for subsequent viewing without the need to refocus onto a curved surface.

The question arises whether the contact area will be large enough to be useful. One can make a crude estimate of the contact area using the classical Hertzian contact stress equations which apply to an elastic cylinder of radius R and length L and modulus E in "line" contact with an elastic semi-infinite medium having a plane surface. Assuming that the properties of the latter are given by those of the glass slide (and not the ~7 micron thick tissue) the properties of the plastic dominate and the relevant parameter is approximately 1/E.

The contact pressure p is given by $p=p_0(1-y^2/b^2)^{1/2}$ where $p_0 \sim =\frac{1}{2}(PE/RL)^{1/2}$. The contact semi-width b is given by $b \sim =(PR/EL)^{1/2}$. Using values of 2R=3/16 inch, L=1 mm, P=1 lb, and $E=10^5$ psi, b is 125 microns, and $p_0$ is 2500 psi. If P=1 oz, then b=30 microns, and $p_0$=625 psi. If E is $10^4$ psi (a possibility), then $b \sim =400$ microns and $p_0 \sim =800$ psi for P=1 lb, and b=100 microns and $p_0$=200 psi for P=1 oz.

Thus it appears as if the "line" contact area will be large enough to be useful and small enough so that adjacent samples on the periphery can be kept separate. However, these calculations are to be taken with care since the EVA film used for the preferred coating may deform plastically in cases of high contact stress which would tend to increase the contact area, as would taking the tissue properties into account. On the other hand the compliant elastic is only in a thin film on a relatively rigid cylinder which would tend to make the contact area smaller. Our experiments indicate that with reasonable contact forces, the desired area can be obtained.

Since the theoretical stress distribution is parabolic (which will be smoothed out by deviations from the ideal Hertzian model), the question arises as to whether the stress can be controlled well enough so that it allows good transfer but does not cause nonspecific pickup. (This situation is no worse than the existing situation with flat geometries—it is just more explicit since it is easier to "analyze".) Once again, our experiments indicate that this is possible. We frequently use a contact force of 1 gm which leads to a maximum pressure $p_0$ of ~40 psi and a b of ~20$\mu$.

The situation is simpler with the polygonal cross section rods. If a facet is 1 mm long in the peripheral direction and 1 mm wide in the rod axial direction, then the contact area is $\frac{1}{625}$ inches$^2$. If the contact force is 1 oz and the contact stress is assumed to be uniform (due to the flat surface), then its value is $\frac{1}{16}$ lb/$\frac{1}{625}$ in$^2$=40 lb/in$^2$ psi, a value that is known to give good results.

The issue of alignment of the contact surface with the tissue sample is relevant. Assume that the rod is relieved so that only a 1 mm length of it (where the film is deposited) is in contact with the tissue. Assume that the mechanical mechanism has been adjusted so that everything is perfectly aligned i.e., the contact surface is exactly parallel to the slide when it has been lowered to touch the slide so that the gap between the two uniformly vanishes. In a preliminary design, the relevant pivot point for the lift off of the rod is approximately 4 inches from the contact point with the tissue. Even if the pivot point shifts 0.005 inches vertically due to operation of the mechanism, (unlikely in a reasonably good mechanism), the change in the contact angle will only be ~0.00125 radians. Taken over the 1 mm (1000 micron) length of the film contact area, this minute change in contact angle causes only slightly more than 1 micron change in elevation of the film off the tissue. This is within the anticipated nonuniformities in the film and tissue and would not have a significant effect.

Having set forth the physics related to the contact of coated collection tip T on sample collecting rod R with sample A on slide S, some attention can be devoted to the particular configurations which could be used at coated collection tip T at the end of sample collecting rod R.

Figure 3:
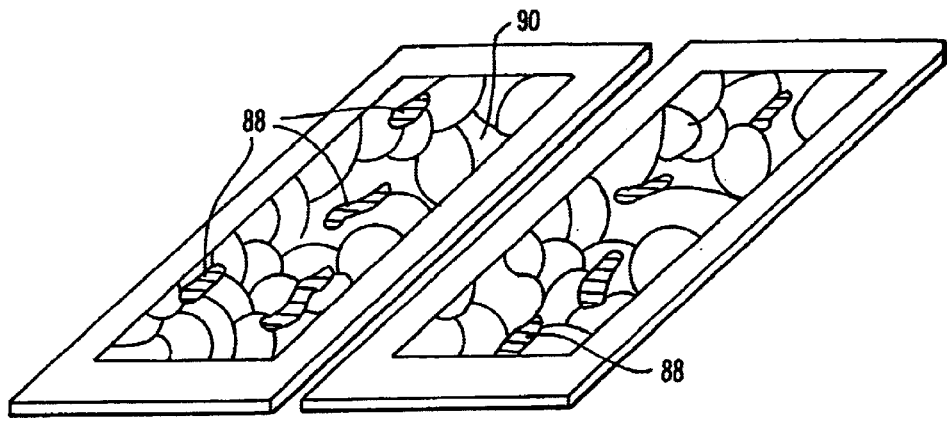
FIG. 3 is a view of two typical slides side-by-side each of which contains tissue samples illustrating cell locations on the slides remote from one another for collection by the convex geometry adhesive film system.

Referring to FIG. 3, the overall problems to which the disclosure is directed can be discussed. Slide $S_1$ having sample $A_1$ is shown along side slide $S_2$ having sample $A_2$. Examining the illustrated (and over-simplified illustrated samples) desired cells 88 are shown interspersed with undesired cells 90. The reader will understand that the real biological world is vastly more complex then this illustration. However that may be, using these slides and referring to the collection apparatus and method here set forth, three important observations about this disclosure can be made.

First, where desired cells 88 are collected, the problem is frequently collecting sufficient amounts of the desired cells for further analysis. In the illustrated slides, it is to be understood that collection of one of the three groups of desired cells 88 may produce insufficient quantity for further testing. Further, observing both slides, the cells present on one slide may not be sufficient; collection of cells from a second sample $A_2$ on a second slide $S_2$ or additional slides may be required. Thus, a single collection tip T can effectively concentrate many rarely occurring cells from a large amount of histological tissue. Further, collection on more than one coated collection tip T can occur. Simply stated, the process of collection of desired cells 88 can continue until the desired amount is present and ready for testing.

Figure 4A:
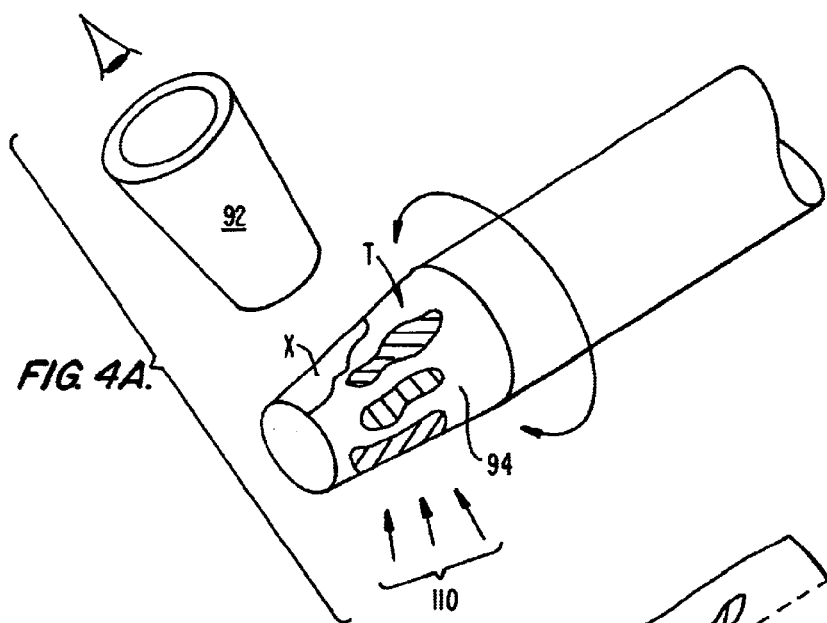
FIG. 4A is a perspective view of a frustum-shaped surface having the desired cells collected on the selectively activated film on the frustum surface, with the view schematically showing inspection of the collected samples by the microscope.
Figure 4B:
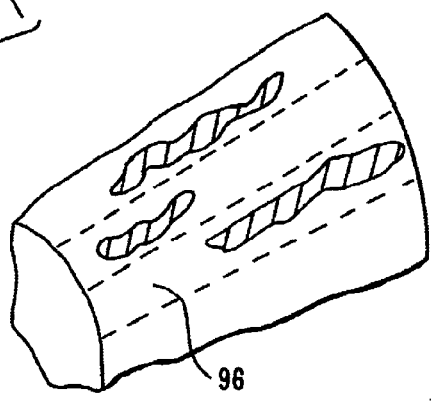
FIG. 4B is a magnified view of the collection surface of FIG. 4A illustrating the large numbers of samples that can be collected upon a single convex surface.

Secondly, referring to FIGS. 4A and 4B, it will be understood that the convex surface concept here disclosed is an ideal way to collect and concentrate such cells. Referring to FIG. 4A, an exaggerated collection of desired cells 88 on coated collection tip T is shown. Referring to FIG. 4B, a denser concentration of desired cells 88 is shown. In actual fact, it is contemplated that typically 30 such samples can be collected around the periphery of the coated collection tip T. This should assure collection of sufficient sample for further testing.

Third, once the desired cells 88 are collected on coated collection tip T, they may thereafter be inspected before further processing. For example, a pathologist may not want to undertake the tedium (albeit reduced tedium) required for the cell collection. At the same time, that pathologist knows the exact nature of desired cells 88 for collection. Once a technician has collected the cells, inspection of the cells on coated collection tip T can be performed by a pathologist or other technical person. This would typically occur under an inverted microscope $M_I$—but is schematically shown here at eye loop 92.

It may well be that certain collected specimens may fail to pass such inspection. These specimens can be prevented from subsequent processing either by precision encapsulation using the laser to remelt the adhesive, or by destruction through irradiation e.g., UV to destroy DNA or an intense focal heat pulse with a laser. This is illustrated by post attachment treatment 110 in FIG. 4A.

It will be understood that liberation of at least part of desired cells 88 can occur by many convenient expedients. For example, dissolving the protein present in the cells can liberate DNA and RNA present for further testing.

Confining attention to coated collection tip T shown in FIG. 4A, a general discussion can be made. Coated collection tip T includes an underlying convex surface X overlying convex surface X, coating 94 is shown. Some general discussion about coating 94 is in order.

First, coating 94 must be capable of activation to produce the desired adhesion qualities desired. Second, coating 94 must be capable of adhering to convex surface X. Third, it is desirable that sample collecting rod R at convex surface X be transparent. This enables conventional transmission observation of desired cells 88 of sample A during all stages of the collection procedures.

Thermoplastic polymer films are widely used as heat-and pressure-activated adhesives for bonding surfaces. Most of these polymer films are transparent or translucent to visible light used in conventional light microscopy. These films are, however, strongly absorptive in specific regions of the electromagnetic spectrum (e.g., in regions of the infrared associated with strong molecular vibration modes such as 3000, 1800, 1400–960 cm$^{-1}$).

The activatable adhesive film 94 may be made of a wide variety of electromagnetically or thermally activatable materials, such as ethylene vinyl acetate (EVA), polyurethanes, polyvinyl acetates, and the like. Specific other selectively activatable materials found useful in the practice of the invention are: thermal sensitive adhesives and waxes, such as Precision Coatings product #HAL-2 180C;

thermally-activated hot glues and sealants, such as those from Ban Fastening Systems (Brooklyn, N.Y.); ultraviolet sensitive or curing optical adhesives, such as ThorLabs, Inc. product N060-N0A81; thermal or optical emulsions, such as silkscreen coated emulsion B6, high mesh powdered, reconstituted lelt fixit emulsion (Riso Kagaku Corp.) and various other compounds including acetal, acrylic, alloys and blends, allyl, bismaleimides, cellulosics, epoxy, fluoroplastics, ketone-based resins, liquid crystal polymers, melamine-formaldehyde, nitrile, nylon, phenolic, polyamide, polyacrylate, polybenzimidazole, polybutylene, polycarbonate, thermoplastic polyester, liquid crystal polymers, polybutylene terephthalate (PBT), polycyclohexvlenedimethylene terephthalate (PCT), engineering grade polyethylene terephthalate (PET), standard grade polyethylene terephthalate (PET), thermoset polyetherimide polyethylene polyester, branched polyethylene, ethylene acid copolymer, ethylene-ethyl acrylate (EEA), ethylene-methyl acrylate (EMAC), ethylene-vinyl alcohol copolymers (EVOH), high-density polyethylene, HMW-high-density polyethylene, Ionomer, linear low-density polyethylene, linear polyethylene, low-density polyethylene, UHMW polyethylene, very-low-density polyethylene, thermoplastic polyimide, thermoset polyimide, polymethylpentene, modified polyphenylene oxide, polyphenylene sulfide, blow molding PPS, polyphthalamide, polypropylene, polypropylene homopolymer, polypropylene impact copolymers, polypropylene random copolymers, silicones, styrenic resins, ABS, ACS, acrylic-styrene-acrylonitrile, expandable polystyrene, general purpose polystyrene, impact polystyrene, olefin-modified SAN, polystyrene, styrene-acrylonitrile (SAN) and styrene-butadiene copolymers.

It is also possible to add infrared absorbing dyes to the thermoplastic films 94 to provide strong absorption at other specific infrared wavelengths without altering the films transparency to visible light. Such dyes are preferably IR absorbing dyes which are readily soluble in the plastic films and have a very strong, narrow IR or near-IR absorption bands that can be matched to a variety of IR or near-IR lasers (including particularly laser diodes). If the focused pulse of electromagnetic radiation (e.g., laser) is delivered at wavelengths that are strongly absorbed by the film, then the film may be efficiently focally heated.

Many dye types could be considered for IR absorption, since most classes of visible absorbing dyes can be extended in wavelength by molecular modification. Phthalocyanines and cyanines have been among the most popular dyes because of stability, ease of preparation, solubility, optical and other properties. Moreover, the number of possible modifications of these dyes is very large because various central metal atoms which can be added and a variety of ring attachments which can be made to them. A book which gives a general overview of IR absorbing dyes is:

INFRARED ABSORBING DYES

Masaru Matsuoka, ed. (U. of Osaka, Sakai, Osaka)

Plenum Press NY 1990

0-30843478-4

TA1690.I53 1990 available in the NBS library series: Topics in Applied Chemistry, A. R. Katritzky and G. J. Sabong, eds.

As an example of phthalocyanine dyes, the following 60 entries are in the Aldrich Chemical Catalog:

TABLE 1

PHTHALOCYANINE DYES (Aldrich Chemical Company)

| | | |
|---|---|---|
| #412066 | Name: | TETRAKIS(4-CUMYLPHENOXY)PHTHALO-CYANINE, 97% |
| #404543 | Name: | TIN(II) PHTHALOCYANINE |
| #406481 | Name: | SILICON PHTHALOCYANINE DIHYDROXIDE Cata |
| #414387 | Name: | VANADYL 2,9,16,23-TETRAPHENOXY-29H,31H-PHTHALOCYANINE |
| #393932 | Name: | MANGANESE(III) PHTHALOCYANINE CHLORIDE |
| #410160 | Name: | IRON(II) PHTHALOCYANINE BIS(PYRIDINE) COMPLEX |
| #404551 | Name: | TITANYL PHTHALOCYANINE |
| #418145 | Name: | 1,8,15,22-TETRAPHENOXY-29H,31H-PHTHALOCYANINE |
| #418153 | Name: | 2,9,16,23-TETRAPHENOXY-29H,31H-PHTHALOCYANINE |
| #379573 | Name: | IRON(III) PHTHALOCYANINE CHLORIDE Catal |
| #406473 | Name: | TIN(IV) PHTHALOCYANINE DICHLORIDE Catal |
| #415448 | Name: | NICKEL(II) TETRAKIS (4-CUMYLPHENOXY) PHTHALOCYANINE |
| #418161 | Name: | 1,8,15,22-TETRAKIS (PHENYLTHIO)-29H,31H-PHTHALOCYANINE |
| #418188 | Name: | 2,9,16,23-TETRAKIS (PHENYLTHIO)-29H,31H-PHTHALOCYANINE |
| #408808 | Name: | GALLIUM(III) PHTHALOCYANINE CHLORIDE Ca |
| #418986 | Name: | ALUMINUM 2,9,16,23-TETRAPHENOXY-29H, 31H-PHTHALOCYANIN |
| #310204 | Name: | COPPER(II) 4,4',4'',4'''-TETRAAZA-29H,31H-PHTHALOCYAN |
| #402737 | Name: | MAGNESIUM PHTHALOCYANINE |
| #402745 | Name: | DISODIUM PHTHALOCYANINE |
| #418250 | Name: | ALUMINUM 2,9,1 |
| #341169 | Name: | ZINC PHTHALOCYANINE |
| #379557 | Name: | MANGANESE(II) PHTHALOCYANINE Catalog Nu |
| #414379 | Name: | NICKEL(II) 2,9,16,23-TETRAPHENOXY-29H,31H-PHTHALOCYAN |
| #433462 | Name: | METHYLSILICON( |
| #418234 | Name: | ZINC 2,9,16,23-TETRAKIS(PHENYLTHIO)-29H, 31H-PHTHALOCY |
| #418242 | Name: | ALUMINUM 1,8,1 |
| #379549 | Name: | IRON(II) PHTHALOCYANINE |
| #408875 | Name: | LEAD(II) TETRAKIS (4-CUMYLPHENOXY) PHTHALOCYANINE |
| #393894 | Name: | VANADYL 3,10,17,24-TETRA-TERT-BUTYL-1,8, 15,22-TETRAKI |
| #432946 | Name: | COPPER(II) TET |
| #441082 | Name: | GALLIUM(III) P |
| #423157 | Name: | 2,9,16,23-TETR |
| #393886 | Name: | COPPER(II) 3,10,17,24-TETRA-TERT-BUTYL-1,8,15,22-TETR |
| #418269 | Name: | ALUMINUM 1,8,1 |
| #423165 | Name: | COPPER(II) 2,9 |
| #430994 | Name: | ZINC 2,9,16,23 |
| #307696 | Name: | COBALT(II) PHTHALOCYANINE Catalog Number |
| #432180 | Name: | SILICON 2,9,16 |
| #446637 | Name: | ALUMINUM PHTHA |
| #253103 | Name: | 29H,31H-PHTHALOCYANINE,98% Catalog Number |
| #379565 | Name: | LEAD(II) PHTHALOCYANINE |
| #418277 | Name: | ALUMINUM 2,9,1 |
| #362530 | Name: | ALUMINUM PHTHALOCYANINE CHLORIDE Catalo |
| #444529 | Name: | ZINC 1,2,3,4,8 |
| #452521 | Name: | IRON(III) PHTH |
| #446645 | Name: | COBALT(II) 1,2 |
| #446653 | Name: | COPPER(II) 1,2 |
| #448044 | Name: | IRON(II) 1,2,3 |
| #386626 | Name: | ALUMINUM 1,4,8,11,15,18,22,25-OCTABUTOXY-29H,31H-PHTH |
| #360635 | Name: | NICKEL(II) PHTHALOCYANINE Catalog Number |
| #448311 | Name: | COPPER(II) 1,2 |
| #428159 | Name: | SILICON(IV) PH |
| #386618 | Name: | COPPER(II) 1,4,8,11,15,18,22,25-OCTABUTOXY-29H,31H-PH |
| #287768 | Name: | SILICON PHTHALOCYANINE DICHLORIDE Catal |
| #408883 | Name: | NICKEL(II) 1,4,8,11,15,18,22,25-OCTABUTOXY-29H,31H-PH |

TABLE 1-continued

PHTHALOCYANINE DYES (Aldrich Chemical Company)

| | | |
|---|---|---|
| #383813 | Name: | ZINC 1,4,8,11,15,18,22,25-OCTABUTOXY-29H,31H-PHTHALOC |
| #362549 | Name: | DILITHIUM PHTHALOCYANINE |
| #383805 | Name: | 1,4,8,11,15,18,22,25-OCTABUTOXY-29H,31H-PHTHALOCYANIN |
| #252980 | Name: | COPPER(II) PHTHALOCYANINE Catalog Number |
| #245356 | Name: | COPPER(II) PHT |

An example of a traditional near-IR absorbing dye, also used for diagnostic purposes, is Aldrich #22886-9 dye, indocyanine green. Another, used as a biological stain, is Aldrich #11991-1, naphthol green B. Of all these dyes, a particularly good choice for this application are the naphthalocyanine dyes which have low water solubility but high solubility in nonpolar polymers. For example, vanadyl 5,14,23,32-tetraphenyl 2,3-naphthalocyanine [Aldrich 39,317-7 (CA 131220-68-3)] with a molecular formula weight of 1084 daltons exhibits a strong absorption peak (with a molar extinction coefficient of ~200,000 at 846 nm) and,high solubility in ethylene vinyl acetate (EVA) low melting polymers (such as Dupont ELVAX™ 410). This dye absorption peak matches well the emission wavelength of selected GaAlAs laser diodes. Similarly, vanadyl 2,11,20,29-tetra-tert-butyl-2,3-naphthalocyanine [CA 105011-00-5] FW1004 absorbs near IR with a narrow peak at 808 nm which closely matches the emission wavelength (selected by choosing a different value of [Al]) of GaAlAs laser diodes widely used to pump solid state Nd:YAG lasers. All these naphthalocyanine dyes (Table 2) are highly soluble in EVA polymer thermoplastics and other similar thermoplastic materials. They are quite stable compounds particularly with heating to ~300° C. and do not exhibit adverse photochemistry which might affect biological macromolecules in the tissue.

A table of naphthalocyanine dyes as presented in the Aldrich Catalog is presented below:

TABLE 2

NAPHTHALOCYANINE DYES (Aldrich Chemical Company)

1) vanadyl 5,14,23,32-tetraphenyl 2,3-naphthalocyanine
Aldrich 39,317-7CA 131220-68-3FW1084 846nm p. 104
2) tin(IV) 2,3-naphthalocyanine dichloride
Aldrich 40,651-1CA 26857-61-4 FW902 828nm p. 102
3) silicon(IV) 2,3-naphthalocyanine dihydroxide
Aldrich 40,653-8CA 92396-90-2 FW775 785nm p. 94
4) silicon(IV) 2,3-naphthalocyanine dioctyloxide
Aldrich 40,767-4CA 92941-50-9 FW941 798nm p. 94
5) 5,9,14,18,23,27,32,36-octabutoxy 2,3-naphthalocyanine
Aldrich 41,207-4CA 105528-25-4FW1292 867nm p. 181
6) copper(II) 5,91,14,18,23,27,32,36-octabutoxy 2,3-naphthalocyanine
Aldrich 41,528-6CA 155773-67-4FW 853nm p. 33
7) nickel(II) 5,9,14,18,23,27,32,36-octabutoxy-2,3-naphthalocyanine
Aldrich 41,885-4CA 155773-70-9FW1348 848nm p. 78
8) vanadyl 2,11,20,29-tetra-tert-butyl-2,3-naphthalocyanine
Aldrich 43,296-2CA 105011-00-5FW1004 808nm p. 1524 '96

The interaction of laser beam Z or other activating light source is shown in FIG. 1. Most conveniently, most conventional microscopes have provision for introducing such epi-illumination to the sample. Activating light—such as laser Z—can be conveniently introduced in such light paths.

A variety of wavelengths of electromagnetic energy can be used in the practice of the invention provided that suitable materials are used. In particular, it is important that the transfer film 94 absorb sufficient energy (or contain one or more dyes that absorb sufficient energy) at the chosen wavelength to melt or nearly melt the thermoplastic polymer in the targeted region. For thermoplastic materials such as ethylene vinyl acetate (EVA), a wavelength of about 3 to about 10 micrometers is preferred as these materials intrinsically absorb in this range. In one embodiment, the power of the laser is used generally in the range of from about 1 mW to about 200 mW depending on the size of the target (i.e, increasing power with increasing target size). It is also preferred that the wavelengths for laser activation and film absorption be chosen outside the normal range used for microscopic imaging. Reproducible microtransfer of tissue can be obtained using a variety of infrared wavelengths from the laser.

Suitable lasers for use in the present invention include carbon dioxide lasers (9.6–11 μm wavelengths), laser diodes, tunable single frequency Ti:sapphire lasers and diode-pumped NdYAG lasers. The wavelength outputs from these lasers can preferably range from ultraviolet to infrared. A particularly desirable laser for use with the present invention is the laser diode with wavelengths between 690 and 1300 nm. In this wavelength range, conventional glass microscope optics is highly transmissive and can be used to focus the laser. This is a marked improvement over laser capture microdissection designs using longer laser wavelengths (e.g., 9.6–11 μm) for the carbon dioxide laser or ~3 μm with the Er:YAG with laser diode pumping or- intrinsic).

Referring to FIGS. 4B, an important feature of this invention may be observed. Specifically, the footprint of contact of coated collection tip T with sample A can be larger than the footprint of desired cells 88 of sample A. By the expedient of activating coated collection tip T only in the profile of the footprint of desired cells 88, precise collection can occur. Thus, not all cells within the contact area are necessarily removed. This is what is shown in FIGS. 4A and 4B.

Further, and from the discussion above, it will be understood that two features can control the footprint of contact (as distinguished from the footprint of activation) of coated collection tip T with sample A. First, and as discussed above, the force of contact will in some measure control the size of the footprint of contact 96 illustrated between the broken lines of FIG. 4B.

Second, the particular shape of the convex surface can likewise control the size of the footprint of contact. For this, reference is made to FIGS. 5A–5E. It is assumed that the contact surface is substantially parallel (at least locally) to the surface of sample A.

Figure 5A:
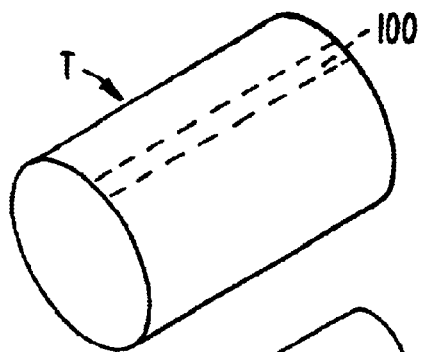
FIG. 5A–5E is a series of illustrations setting forth possible convex geometries that can be placed on the sample with, FIG. 5A illustrating a cylinder, FIG. 5B illustrating a portion of an oblate spheroid, FIG. 5C illustrating a portion of a sphere, FIG. 5D illustrating a portion of a sphere having facets, FIG. 5E illustrating a frustum having facets.

FIG. 5A represents coated collection tip T having a right cylindrical shape. Depending upon force applied, cylindrical contact footprint 100 is either a straight line or a rectilinear patch. Given the angularity of sample collecting rod R with respect to sample A, such a surface is not desired.

Figure 5B:
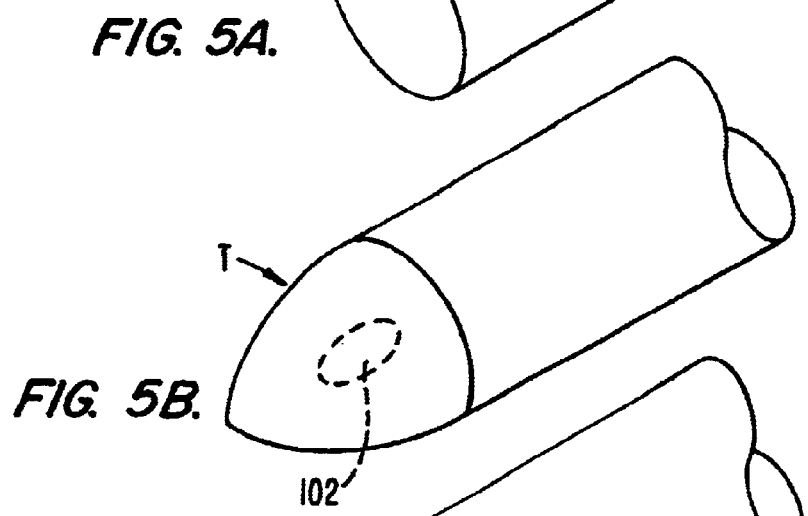

FIG. 5B illustrates coated collection tip T having the profile of one half of an oblate spheroid (football shaped). Such a coated collection tip T has a roughly elliptical contact profile 102.

Figure 5C:
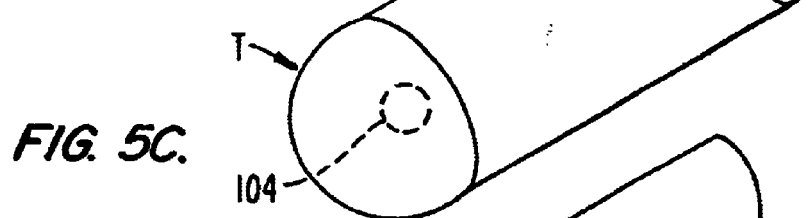

FIG. 5C illustrates coated collection tip T having a spherical surface. Such a coated collection tip T would have a circular contact profile 104—which upon reduction of the contact force would effectively reduce to a point.

Figure 5D:
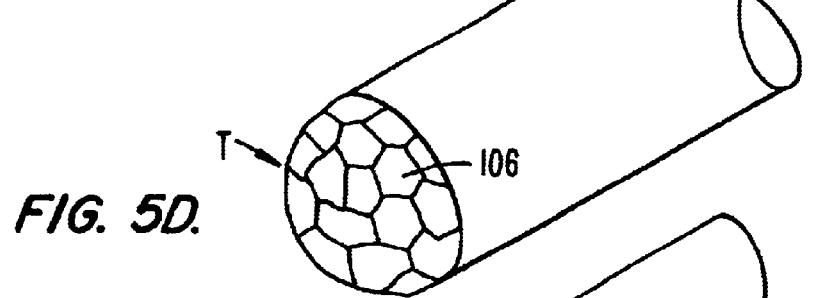

FIG. 5D illustrates coated collection tip T having a faceted sphere with discrete facets 106. Such discrete facets 106 would themselves define the contact area.

Figure 5E:
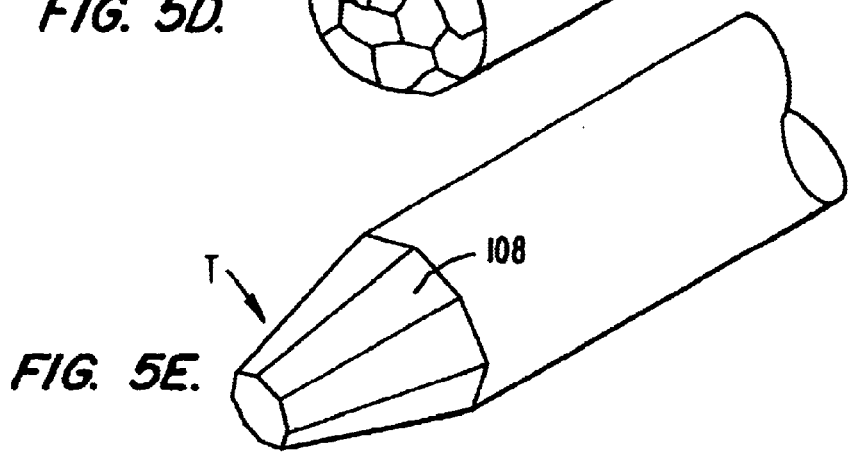

FIG. 5E includes a coated collection tip T having planar facets 108 extending along the length of the cone. Again, the facets will define the area of contact with sample A.

It will be understood that once convex surface X is produced, the coating of the selectively activatable adhesive on the contact surface can be made in any manner desired. For example, dipping convex surface X into a solution which upon drying or curing forms the required coating will suffice for the practice of this invention. Alternatively, forming the coating in a specially contoured mould cavity can be done using molten material attached to the outside of the convex surface, which then is placed inside the cavity.

Referring to FIG. 6A, dip coating sample collecting rod R with activatable adhesive is done by mounting it in a suitable schematically shown rotating device 112, inserting the rod vertically with rotation down into heated solution 114 of 20% weight/volume EVA (DuPont Elvax 410) in tetrachloroethylene so the tip is immersed to the desired depth of coating, and withdrawing the rod. Sample collecting rod R is then moved to a horizontal position with continued rotation and the solvent allowed to evaporate. A draft of air, such as conducting the operation in a hood, is desirable. A suitable angle of positioning the rod other than exactly horizontal may be desired for best distribution of the coating, and it may be desirable to remove solution from the end of the rod before evaporation. The temperature of the solution can be varied and, as an example, 50 degrees C. can be used. Multiple coatings can be made to obtain a desired thickness, and two or three coats, made with evaporation between dipping, are done. Coating 94 on sample collecting rod R results as shown in FIG. 6B.

It is found desirable in many instances to impress the coated rod R within a specially contoured mould cavity 111 whose concave contour will produce the desired convex surface. The coating or the, mould or both should be heated to accomplish this shaping operation.

As shown methods of coating include dipping the rod (see FIGS. 6A), spraying at nozzle 116 the solution on the rod (see FIG. 7), and adding controlled volumes of solution to the rod with micropipet 118 (see FIG. 8). Each of these methods of coating the rod with solution are followed by evaporation of the solvent, and with each method, rotation of the rod during addition of the solution and evaporation is desirable by schematically shown rotating device 112.

Solutions of hot-melt adhesive can be made in a variety of solvents. For the ethylene vinyl acetate (EVA) used, toluene (109-88-3) and a variety of chlorinated hydrocarbon solvents can be used. Examples of chlorinated solvents which can be used are methylene chloride (75-09-2), carbon tetrachloride (56-23-5), chloroform, (67-66-3), tetrachloroethane (630-20-6), tetrachloroethylene (127-18-4), trichloroethylene (79-01-6) and 1,1,1-trichloroethane (71-55-6). It would be expected that other solvents used for polymer and vinyl solutions would be suitable. The choice of solvent is dictated by considerations of safety, solvent effectiveness, and volatility. The latter is particularly important, in matching-volatility to the effectiveness of the process and characteristics of the coating such as evenness, smoothness, depth of coating and rate of drying.

Solutions of EVA can be made in various concentrations and higher concentrations, above 15% or 20% weight/volume for some solvents, must be heated above room temperature to remain liquid. The optimum concentration depends on the coating method, for example spraying works best with lower concentrations and higher concentrations are best for dipping. An advantage of dipping with higher concentrations of solution, which are heated to remain liquid, is that the cooling of the coating on the rod results in deposition of a thick film.

Rotation of the rod during coating and evaporation is desirable to get best distribution of the coating.

Film coatings of a few microns (micrometers) to 100 or more microns (0.004 inches) can be obtained by these methods. After drying of the solvent, the coating can be smoothed by heat treatment or shaping in a mold.

In the following claims we utilize the words "convex." It is to be understood by this designation that we include all surfaces which place a central portion in contact with the slide and film and have peripheral surfaces away from contact with the slide. It will be understood that at least part of the surface—whether in contact with the slide or not in contact with the slide—impresses the selectively activated surface onto the sample. Upon activation this produces adhesive regions. Thus, the adhesive regions are bordered by either non-activated or selectively activated surfaces which are away from that contact. Thus, upon reorientation, the peripheral regions can be utilized for activation and collection.

We therefore include convex surfaces which are spheres, oblate spheroids (football shapes), cones, frustum shapes (truncated cones), cylinders, and the like.

It will further be understood that all of the above surfaces can be faceted. We therefore include such faceted surfaces placed on "convex" shapes.

What is claimed is:

1. In an apparatus for laser laser capture microdissection, a contact surface comprising:

a convex surface for placement to a sample;

a rod with the convex surface mounted to an extremity of the rod; and, a selectively activated coating placed over the convex surface having non-adhesive properties which can be activated to provide selected regions thereof with adhesive properties when placed to a sample while nonactivated regions thereof remain with the non-adhesive properties.

2. The apparatus for laser capture microdissection according to claim 1 wherein:

the convex surface is spherical.

3. The apparatus for laser capture microdissection according to claim 1 wherein:

the convex surface is faceted.

4. The apparatus for laser capture microdissection according to claim 1 wherein:

the convex surface is cylindrical.

5. The apparatus for laser capture microdissection according to claim 1 wherein:

the convex surface has the profile of a frustum.

6. The apparatus for laser capture microdissection according to claim 1 wherein:

the rod and convex surface are transparent.

7. In an apparatus for laser capture microdissection, a contact surface and vial comprising:

a convex surface;

a selectively activated coating placed over the convex surface having non-adhesive properties which can be activated to provide selected regions thereof with adhesive properties when placed to a sample while nonactivated regions thereof remain with the non-adhesive properties;

a vial having a dimension for permitting the convex surface to be placed into the vial; and, a fluid in the vial for liberating at least part of the tissue sample adhered to the selectively activated convex surface.

* * * * *